United States Patent [19]

Alt

[11] Patent Number: 4,622,061

[45] Date of Patent: Nov. 11, 1986

[54] HERBICIDAL 2-HALOACETAMIDES

[75] Inventor: Gerhard H. Alt, University City, Mo.

[73] Assignee: Monsanto Company, St. Louis, Mo.

[21] Appl. No.: 491,477

[22] Filed: May 4, 1983

Related U.S. Application Data

[63] Continuation of Ser. No. 133,759, Mar. 25, 1980, abandoned.

[51] Int. Cl.$^4$ .................... A01N 37/22; A01N 43/08; C07C 103/38; C07D 307/06
[52] U.S. Cl. ........................................... 71/88; 71/98; 71/105; 71/118; 558/414; 549/493; 564/212
[58] Field of Search .................... 71/118, 88, 98, 105; 564/212; 549/493; 260/465 D

[56] References Cited

U.S. PATENT DOCUMENTS

| | | | |
|---|---|---|---|
| 3,268,584 | 8/1966 | Olin | 71/118 X |
| 3,475,157 | 10/1969 | Olin | 71/118 |
| 3,819,661 | 6/1974 | Maravetz | 549/493 |

*Primary Examiner*—Catherine L. Mills
*Attorney, Agent, or Firm*—William I. Andress

[57] ABSTRACT

The disclosure herein relates to 2-haloacetamides substituted on the amide nitrogen atom with certain specific alkenyl or heterocyclic aromatic radicals. These acetamides are useful as herbicides.

27 Claims, No Drawings

HERBICIDAL 2-HALOACETAMIDES

This is a continuation of application Ser. No. 133,759, filed Mar. 25, 1980, now abandoned.

BACKGROUND OF THE INVENTION

1. Field of the Invention

The invention herein pertains to the field of herbicides. More particularly, the field of this invention pertains to the use of 2-haloacetamides as herbicides.

2. Description of the Prior Art

It is known in the prior art to use various 2-haloacetamides as herbicides, either individually or in combination with other herbicides.

Among herbicidal compounds of the prior art are those acetamides having in varying arrangements substitutions of alkyl, cycloalkyl, alkenyl, cycloalkenyl, alkoxy, halogen, aryl, etc. groups, all of which may be further substituted with other radicals.

Illustrative of the 2-haloacetamides of the prior art and of those most closely related in structure to the 2-haloacetamides disclosed and claimed herein are those disclosed in U.S. Pat. Nos. 2,929,702, 3,690,864 and 4,155,744, Canadian Pat. No. 779,917 (related in part to U.S. Pat. No. 3,287,106) and South African Pat. No. 753,918. Among the numerous substituents that may be substituted on the amide nitrogen atom are an alkenyl radical ('702, '864, '917, '106 and '918 patents) or a cycloalkenyl radical ('744 patent). In addition, a second substituent on the amide nitrogen may be a heterocyclic radical ('702 patent), an aralkylene radical having at least three carbon atoms in the alkylene moiety ('864 patent) or an alkoxyalkyl radical ('106 and '918 patents).

As will be apparent from the many combinations and permutations of radicals which may be included on the amide nitrogen, none of the prior art compounds including those most closely related in structure include 2-haloacetamides which may be substituted simultaneously on amide nitrogen atom with the particular combinations of alkenyl, polyalkoxy, heterocyclic or aromatic radicals disclosed and claimed herein.

SUMMARY OF THE INVENTION

The present invention relates to herbicidally active compounds, herbicidal compositions containing these compounds and herbicidal method of use of said compositions in agricultural crops, e.g., in dicotyledonous crops such as sugarbeets and soybeans and in monocotyledonous crops such as wheat, sorghum and rice.

The herbicidal compounds of this invention are characterized by the formula

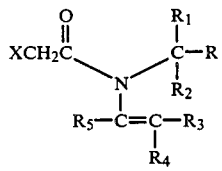

wherein X is chlorine, bromine or iodine;

$R_1$ and $R_2$ are hydrogen or $C_{1-6}$ alkyl;

$R_3$ and $R_4$ are an $R_1$ member or $C_{2-8}$ alkenyl or alkynyl radical;

$R_5$ is an $R_3$ member, phenyl, benzyl or saturated or unsaturated heterocyclic radical containing from 1-3 O, $S(O)_a$ or $N(R_6)_b$ hetero moieties, where $R_6$ is an $R_1$ member or $C_{1-6}$ acyl radical, a is o, 1 or 2 and b is o or 1 or said $R_5$ members substituted with an $R_3$ member, $C_{1-6}$ alkoxy, polyalkoxy, alkoxyalkyl, alkylthio, alkylthioalkyl, nitro, cyano, halogen, trifluoromethyl or hydroxy group and R is a phenyl or heterocyclic radical or substituted phenyl or heterocyclic radical as defined for $R_5$; provided that when R is said heterocyclic or substituted heterocyclic radical, $R_5$ is other than hydrogen, alkyl or alkenyl.

Preferred compounds within the above formula are those wherein $R_1$–$R_4$ members are independently hydrogen or $C_{1-6}$ alkyl, R is a heterocyclic or substituted heterocyclic and $R_5$ is a phenyl or substituted phenyl radical.

Preferred species within the above formula are the following compounds:

N-furfuryl-N-(1-o-tolyl propen-1-yl-2-chloroacetamide,

N-(4-methoxybenzyl)-N-(2-methyl-2-buten-3-yl)-2-chloroacetamide

The above compounds are used singly or in combination as the active ingredient(s) in herbicidal compositions to control undesirable vegetation in important crops.

DESCRIPTION OF PREFERRED EMBODIMENTS

The compounds according to this invention are suitably prepared by reacting the appropriate imine or amine with a haloacylating agent. The starting imine or amine is suitably prepared by reacting the appropriately-substituted ketone with the appropriately-substituted amine.

In specific working embodiments, the preparation of exemplary compounds of this invention will be described in Examples 1–3 below; the same general procedure was followed in order to prepare the compounds of Examples 5–8, but substituting the appropriate starting materials, solvents, reaction conditions, etc., required to obtain the designated product of each example.

EXAMPLE 1

Part (A) of this example describes the preparation of the imine raw material used in Part (B) to prepare the final product.

A. α-Methylbenzyl amine (0.1 mol) and 3-methyl-2-butanone (0.1 mol) were mixed in cyclohexane and heated at reflux temperature under a Dean and Stark trap until no more water was given off. The solvent was then stripped yielding 19 gm of yellow oil identified as N-(α-methylbenzyl)-3-methyl-2-butylimine.

B. A mixture of the imine prepared above (0.05 mol) in 30 ml of toluene and chloroacetyl chloride (0.055 mol) in 40 ml of toluene were heated at reflux for 7 hours; the solvent was then stripped and vacuum distilled to yield 5.0 gm of product, b.p. 158°–162° C./0.4–0.5 mm Hg.

| Anal. for $C_{15}H_{20}ClNO$ (%): | | |
|---|---|---|
| Element | Theory | Found |
| C | 67.79 | 67.72 |
| H | 7.59 | 7.38 |
| N | 5.27 | 5.25 |
| Cl | 13.34 | — |

The product was identified as N-(α-methylbenzyl)-N-(2-methyl-2-buten-3-yl)-2-chloroacetamide.

EXAMPLE 2

The general procedure in Part (A) of Example 1 was followed to prepare N-furfuryl-1-o-tolyl-2-butylimine starting material. A mixture of 0.066 mol of the starting imine in 30 ml of toluene were added 0.07 mol of chloroacetyl chloride in 40 ml of toluene; this mixture was heated under reflux for 5 hours, the solvent stripped and product vacuum distilled to yield 10.5 g of an amber oil, b.p. 173°–175° C./0.2 mm Hg.

| Anal. for $C_{17}H_{18}ClNO_2$ (%): | | |
|---|---|---|
| Element | Theory | Found |
| C | 67.21 | 67.01 |
| H | 5.97 | 6.03 |
| N | 4.61 | 4.60 |
| Cl | 11.67 | 11.60 |

The product was identified as N-furfuryl-N-(1-o-tolylpropen-1-yl)-2-chloroacetamide.

EXAMPLE 3

A mixture of N-(4-methoxybenzyl)-3-methyl-2-methylbutylimine (0.05 mol), prepared similarly as in Part (A) of Example 1, in 20 ml of toluene were mixed with chloroacetyl chloride (0.055 mol) in 50 ml of toluene; this mixture was heated at reflux for 6 hours, the solvent stripped and product distilled in vacuo to yield 11.2 g of amber oil, b.p. 177–180/0.1 mm Hg.

| Anal. for $C_{15}H_{20}ClNO_2$ (%): | | |
|---|---|---|
| Element | Theory | Found |
| C | 63.94 | 63.15 |
| H | 7.15 | 7.19 |
| N | 4.97 | 5.01 |
| Cl | 12.58 | 12.69 |

The product was identified as N-(4-methoxybenzyl)-N-(2-methyl-2-buten-3-yl)-2-chloroacetamide.

EXAMPLES 4–7

Following substantially the same procedures described in Examples 1–3, but substituting the appropriate raw materials, reaction conditions, etc., the compounds of Examples 4–7 were prepared; the compounds are identified in Table I with certain physical properties.

TABLE I

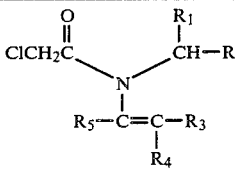

| Example No. | R | $R_1$ | $R_3$ | $R_4$ | $R_5$ | B.P. °C. (mm Hg.) | Element | Theory | Found |
|---|---|---|---|---|---|---|---|---|---|
| 4 |  | H | H | $CH_3$ | 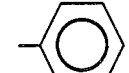 | 174–77 (0.3) | C<br>H<br>N<br>Cl | 66.32<br>5.57<br>4.83<br>12.24 | 66.21<br>5.57<br>4.82<br>12.30 |
| 5 |  OCH₃ | H | $CH_3$ | $CH_3$ | $CH_3$ | 185–187 (0.1) | C<br>H<br>N<br>Cl | 63.94<br>7.15<br>4.97<br>12.58 | 63.47<br>7.01<br>4.81<br>12.37 |
| 6 |  | H | $CH_3$ | $CH_3$ | $CH_3$ | 129–134 (0.05–0.07) | C<br>H<br>N<br>Cl | 66.79<br>7.21<br>5.56<br>14.08 | 66.62<br>7.20<br>5.53<br>14.13 |
| 7 |  OCH₃ | H | $CH_3$ | $CH_3$ | $CH_3$ | 165–169 (0.1–0.15) | C<br>H<br>Cl | 63.94<br>7.15<br>12.58 | 63.82<br>7.20<br>12.89 |

As noted above, the compounds of this invention have been found to be effective as herbicides, particularly as preemergence herbicides, although post-emergence activity has also been shown. Tables II and III summarize results of tests conducted to determine the preemergent herbicidal activity of the compounds of this invention.

The pre-emergence tests are conducted as follows:

A good grade of top soil is placed in aluminum pans and compacted to a depth of three-eighths to one-half inch from the top of the pan. On the top of the soil is placed a predetermined number of seeds or vegetative propagules of various plant species. The soil required to level fill the pans after seeding or adding vegetative propagules is weighed into a pan. A known amount of the active ingredient applied in a solvent or as a wettable powder suspension and the soil are thoroughly mixed, and used as a cover layer for prepared pans. After treatment, the pans are moved into a greenhouse bench where they are watered from below as needed to give adequate moisture for germination and growth.

Approximately 2-3 weeks after seeding and treating, the plants are observed and the results recorded. Table II below summarizes such results. The herbicidal rating is obtained by means of a fixed scale based on the percent injury of each plant species. The ratings are defined as follows:

| % Control | Rating |
| --- | --- |
| 0–24 | 0 |
| 25–49 | 1 |
| 50–74 | 2 |
| 75–100 | 3 |

The plant species utilized in one set of tests, the data for which are shown in Table II, are identified by letter in accordance with the following legend:

| | | |
| --- | --- | --- |
| A Canada Thistle | E Lambsquarters | I Johnsongrass |
| B Cocklebur | F Smartweed | J Downy Brome |
| C Velvetleaf | G Yellow Nutsedge | K Barnyardgrass |
| D Morningglory | H Quackgrass | |

TABLE II

| Compound of Example No. | Kg/ha | Pre-Emergent Plant Species | | | | | | | | | | |
| --- | --- | --- | --- | --- | --- | --- | --- | --- | --- | --- | --- | --- |
| | | A | B | C | D | E | F | G | H | I | J | K |
| 1 | 11.2 | 0 | 1 | 0 | 0 | 3 | 0 | 2 | 0 | 0 | 3 | 3 |
| | 5.6 | 0 | 0 | 0 | 0 | 3 | 0 | 2 | 0 | 0 | 2 | 3 |
| 2 | 11.2 | 0 | 0 | 0 | 0 | 2 | 1 | 3 | 1 | 0 | 3 | 3 |
| | 5.6 | 0 | 0 | 0 | 0 | 1 | 1 | 0 | 0 | 0 | 0 | 3 |
| 3 | 11.2 | 1 | 0 | 0 | 0 | 3 | 1 | 3 | 1 | 0 | 3 | 3 |
| | 5.6 | 0 | 0 | 0 | 0 | 3 | 0 | 0 | 0 | 0 | 1 | 3 |
| 4 | 11.2 | 0 | 0 | 0 | 0 | 3 | 2 | 2 | 1 | 1 | 3 | 3 |
| | 5.6 | 0 | 0 | 0 | 0 | 0 | 0 | 0 | 1 | 0 | 3 | 3 |
| 5 | 11.2 | 2 | 0 | 1 | 1 | 3 | 2 | 3 | 3 | 0 | 3 | 3 |
| | 5.6 | 0 | 0 | 1 | 0 | 2 | 1 | 3 | 3 | 0 | 3 | 3 |
| 6 | 11.2 | 3 | 0 | 1 | 1 | 3 | 3 | 3 | 1 | 0 | 3 | 3 |
| | 5.6 | 0 | 0 | 1 | 0 | 3 | 1 | 2 | 0 | 0 | 3 | 3 |
| 7 | 11.2 | 0 | 0 | 0 | 0 | 3 | 0 | 0 | 1 | 0 | 2 | 3 |
| | 5.6 | 0 | 0 | 0 | 0 | 3 | 0 | 0 | 1 | 0 | 2 | 3 |

The compounds were further tested by utilizing the above procedure on the following plant species:

| | | | |
| --- | --- | --- | --- |
| L | Soybean | R | Hemp Sesbania |
| M | Sugarbeet | E | Lambsquarters |
| N | Wheat | F | Smartweed |
| O | Rice | C | Velvetleaf |
| P | Sorghum | J | Downy brome |
| B | Cocklebur | | |
| Q | Wild Buckwheat | S | Panicum |
| D | Morningglory | K | Barnyardgrass |
| | | T | Crabgrass |

The results are summarized in Table III.

TABLE III

| Compound of Example No. | kg/h | Pre-Emergent Plant Species | | | | | | | | | | | | | | |
| --- | --- | --- | --- | --- | --- | --- | --- | --- | --- | --- | --- | --- | --- | --- | --- | --- |
| | | L | M | N | O | P | B | Q | D | R | E | F | C | J | S | K | T |
| 1 | 5.6 | 0 | 1 | 0 | 2 | 0 | 0 | 3 | 1 | 3 | 1 | 0 | 3 | 3 | 3 | 3 |
| | 1.12 | 0 | 0 | 0 | 0 | 0 | 0 | 0 | 0 | — | 3 | 0 | 0 | 1 | 3 | 3 | 3 |
| | 0.28 | 0 | 0 | 0 | 0 | 0 | 0 | 0 | 0 | 0 | 0 | 0 | 0 | 0 | 0 | 2 | 3 |
| 2 | 5.6 | 0 | 0 | 0 | 0 | 0 | 0 | 0 | 0 | 0 | 0 | 0 | 0 | 3 | 3 | 3 | 3 |
| | 1.12 | 0 | 0 | 0 | 0 | 0 | 0 | 0 | 0 | 0 | 0 | 2 | 0 | 0 | 0 | 3 | 2 |
| | 0.28 | 0 | 0 | 0 | 0 | 0 | 0 | 0 | — | 0 | 0 | 0 | 0 | 0 | 0 | 0 | 0 |
| | 0.056 | 0 | 0 | 0 | 0 | 0 | 0 | 0 | 0 | 0 | 0 | 1 | 0 | 0 | 0 | 1 | 1 |
| 3 | 5.6 | 0 | 1 | 0 | 1 | 3 | 0 | 0 | 0 | 2 | 2 | 2 | 0 | 2 | 3 | 3 | 3 |
| | 1.12 | 0 | 0 | 0 | 0 | 0 | 0 | 0 | 0 | 0 | 1 | 0 | 0 | 0 | 2 | 2 | 3 |
| | 0.28 | 0 | 0 | 0 | 0 | 0 | 0 | 0 | 0 | 0 | 3 | 0 | 0 | 0 | 0 | 1 | 2 |
| | 0.056 | 0 | 0 | 0 | 0 | 0 | 0 | 0 | 0 | 0 | 3 | 0 | 0 | 0 | 0 | 0 | 0 |
| 4 | 5.6 | 0 | 0 | 0 | 0 | 0 | 3 | 0 | 0 | 0 | 2 | 3 | 0 | 3 | 3 | 3 | 3 |
| | 1.12 | 0 | 0 | 0 | 3 | 0 | 1 | 0 | 0 | 3 | 3 | 1 | 0 | 3 | 3 | 3 | 3 |
| | 0.28 | 0 | 0 | 0 | 0 | 0 | 3 | 0 | 0 | 0 | 0 | 0 | 0 | 0 | 1 | 3 | 2 |
| | 0.056 | 0 | 0 | 0 | 1 | 0 | 0 | 0 | 3 | 0 | 0 | 0 | 0 | 0 | 0 | 1 | 1 |
| 5 | 5.6 | 1 | 3 | 3 | 3 | 3 | 0 | 2 | 3 | 3 | 3 | 3 | 1 | 3 | 3 | 3 | 3 |
| | 1.12 | 1 | 2 | 3 | 2 | 3 | 0 | 2 | — | 1 | 3 | 2 | 0 | 3 | 3 | 3 | 3 |
| | 0.28 | 0 | 1 | 1 | 1 | 2 | 0 | 0 | 0 | 1 | 2 | 1 | 0 | 2 | 3 | 3 | 3 |
| | 0.056 | 0 | 1 | 0 | 0 | 1 | 0 | 1 | 0 | 0 | 3 | 0 | 0 | 0 | 2 | 3 | 2 |
| | 0.0112 | 0 | 1 | 0 | 0 | 0 | 0 | 0 | 0 | 0 | 0 | 0 | 0 | 0 | 3 | 2 | 2 |
| 6 | 5.6 | 0 | 1 | 0 | 2 | 1 | 1 | 1 | 1 | 2 | 3 | 3 | 0 | 3 | 3 | 3 | 3 |
| | 1.12 | 0 | 1 | 0 | 1 | 1 | 0 | 0 | 0 | 1 | 2 | 0 | 0 | 1 | 3 | 3 | 3 |
| | 0.28 | 0 | 0 | 0 | 0 | 0 | 0 | 0 | 0 | 0 | 0 | 0 | 0 | 0 | 2 | 3 | 3 |
| | 0.056 | 0 | 0 | 0 | 0 | 0 | 0 | 1 | 0 | 3 | 0 | 0 | 0 | 0 | 0 | 2 | 2 |
| 7 | 5.6 | 0 | 2 | 1 | 2 | 3 | 0 | 3 | 0 | 2 | 3 | 0 | 1 | 3 | 3 | 3 | 3 |
| | 1.12 | 0 | 1 | 0 | 0 | 0 | 0 | 0 | 0 | 3 | 0 | 0 | 1 | 3 | 3 | 3 | 3 |
| | 0.28 | 0 | 0 | 0 | 0 | 0 | 0 | 0 | 0 | 0 | 0 | 0 | 0 | 3 | 3 | 3 | 3 |
| | 0.056 | 0 | 1 | 0 | 0 | 0 | 0 | 0 | 0 | 0 | 3 | 0 | 0 | 0 | 0 | 0 | 1 |

EXAMPLES 8–44

The compounds in the following examples may also be prepared by substantial repetition of the general procedures described in Examples 1–4, modified as to reaction temperatures, times, solvents, etc., to account for the nature of the particular reactants, as will be apparent to those skilled in the art. In Table IV, the individual compounds are those whose members are identified by the generic formula.

TABLE IV $$XCH_2\overset{O}{\underset{\|}{C}}-\underset{\underset{R_5-C=C-R_3}{|}}{N}-\underset{R_2}{\overset{R_1}{\underset{|}{C}}}-R$$
$$\phantom{XCH_2C-N-C-R}\phantom{xxxx}R_4$$

| Cpd. of Ex. No. | X | R | $R_1$ | $R_2$ | $R_3$ | $R_4$ | $R_5$ |
|---|---|---|---|---|---|---|---|
| 8 | Cl | 2-(1,3-oxathiolanyl) | H | H | H | $CH_3$ | phenyl |
| 9 | Cl | 2-(2,3-dihydrofuranyl) | H | H | $CH_3$ | $CH_3$ | phenyl |
| 10 | Cl | 2-(2,3-dihydrofuranyl) | $CH_3$ | H | $CH_3$ | $CH_3$ | $-CH_2-$phenyl |
| 11 | Br | 2-(1,3-oxathiolanyl) | H | H | H | H | 2-methylphenyl |
| 12 | Br | 2-(1,3-oxathiolanyl) | H | H | H | $CH_3$ | 2-methylphenyl |
| 13 | Cl | 2-(1,3-oxathianyl) | H | H | $CH_3$ | $CH_3$ | phenyl |
| 14 | Cl | 2-(2,3-dihydrothienyl) | H | H | H | $CH_3$ | phenyl |
| 15 | Cl | 2-(1,3-dithiolanyl) | H | H | H | $CH_3$ | phenyl |
| 16 | Br | 2-(2,3-dihydrothienyl) | H | $CH_3$ | $CH_3$ | $CH_3$ | phenyl |
| 17 | Cl | 2-(3,4-dihydro-2H-thiopyranyl) | H | H | H | $CH_3$ | $-CH_2-$phenyl |
| 18 | Cl | 2-(2,3-dihydro-1H-pyrrolyl) | H | H | $CH_3$ | $CH_3$ | phenyl |

TABLE IV-continued $$XCH_2\overset{\overset{O}{\|}}{C}-N\overset{\overset{R_1}{|}}{\underset{\underset{R_5-C=C-R_3}{\underset{R_4}{|}}}{\overset{|}{C}-R}}$$

| Cpd. of Ex. No. | X | R | $R_1$ | $R_2$ | $R_3$ | $R_4$ | $R_5$ |
|---|---|---|---|---|---|---|---|
| 19 | Cl | 2-thiazolidinyl (S, NH) | H | H | $CH_3$ | $CH_3$ | phenyl |
| 20 | Cl | thiazinyl (O, S, NH) | H | H | H | $CH_3$ | 2-methylphenyl |
| 21 | Cl | imidazolidinyl | H | H | $CH_3$ | $CH_3$ | phenyl |
| 22 | Cl | imidazolidinyl (NH) | $CH_3$ | H | H | $CH_3$ | 2-methoxyphenyl |
| 23 | Cl | phenyl | $CH_3$ | H | $CH_3$ | $CH_3$ | $CH_3$ |
| 24 | Br | phenyl | $CH_3$ | H | $CH_3$ | $CH_3$ | $CH_3$ |
| 25 | I | phenyl | H | H | $CH_3$ | $CH_3$ | $CH_3$ |
| 26 | Cl | 2,6-dimethoxyphenyl | H | H | $CH_3$ | $CH_3$ | $CH_3$ |
| 27 | Cl | 2-furyl | H | H | $CH_3$ | H | 2-furyl |
| 28 | Cl | 2-(1,3-oxathiolanyl) | H | H | H | H | 2-(1,3-oxathiolanyl) |
| 29 | Cl | $-OCH_2O-C_2H_5$ | $CH_3$ | H | H | H | $CH_3$ |

TABLE IV-continued $$\underset{R_5-\overset{|}{\underset{R_4}{C}}=C-R_3}{XCH_2\overset{O}{\overset{\|}{C}}-\underset{\underset{|}{N}}{\phantom{C}}-\overset{R_1}{\underset{R_2}{\overset{|}{C}}}-R}$$

| Cpd. of Ex. No. | X | R | $R_1$ | $R_2$ | $R_3$ | $R_4$ | $R_5$ |
|---|---|---|---|---|---|---|---|
| 30 | Br | —OCH$_2$—OC$_2$H$_5$ | CH$_3$ | H | H | H | CH$_3$ |
| 31 | I | —OCH$_2$—OC$_2$H$_5$ | CH$_3$ | H | H | H | CH$_3$ |
| 32 | Cl | —OCH$_2$O—i-C$_3$H$_7$ | H | H | CH$_3$ | CH$_3$ | C$_2$H$_5$ |
| 33 | Cl | —OCH$_2$O—n-C$_4$H$_9$ | H | H | CH$_3$ | H | CH$_3$ |
| 34 | Cl | —OCH$_2$O—i-C$_4$H$_9$ | H | H | CH$_3$ | H | n-C$_3$H$_7$ |
| 35 | Cl | —OCH$_2$O—sec-C$_4$H$_9$ | H | H | CH$_3$ | H | CH$_3$ |
| 36 | Cl | —OCH$_2$O—n-C$_5$H$_{11}$ | H | H | H | CH$_3$ | C$_2$H$_5$ |
| 37 | Br | —OCH$_2$—OCH$_3$ | C$_2$H$_5$ | H | C$_2$H$_5$ | C$_2$H$_5$ | C$_2$H$_5$ |
| 38 | Cl | —C$_6$H$_5$ | H | H | H | CH$_3$ | allyl |
| 39 | Br | —C$_6$H$_5$ | H | H | H | CH$_3$ | allyl |
| 40 | Cl | —C$_6$H$_4$-CH$_3$ | CH$_3$ | H | CH$_3$ | CH$_3$ | 2-butenyl |
| 41 | Cl | —C$_6$H$_4$-OCH$_3$ | CH$_3$ | H | H | CH$_3$ | 3-pentenyl |
| 42 | Cl | —C$_6$H$_5$ | H | H | CH$_3$ | CH$_3$ | propargyl |
| 43 | Cl | —C$_6$H$_5$ | H | H | H | 1-1-di-methyl-prop-yn-1-yl | |
| 44 | Cl | —C$_6$H$_5$ | H | H | CH$_3$ | CH$_3$ | 2-butynyl |

The herbicidal compositions of this invention including concentrates which require dilution prior to application contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid or organic origin, water, a wetting agent, a dispersing agent, an emulsifying agent or any suitable combination of these.

The compositions of this invention, particularly liquids and wettable powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl, naphthalene sulfonates, sodium naphthalene sulfonate, and the polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor of anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring an aqueous mixture of a water-insoluble active ingredient and an emulsification agent until uniform and then homogenized to give stable emulsion of very finely-divided particles. The resulting concentrated aqueous suspension is characterized by its extremely small particle size, so that when diluted and sprayed, coverage is very uniform. Suitable concentrations of these formulations contain from about 0.1-60% preferably 5-50% by weight of active ingredient, the upper limit being determined by the solubility limit of active ingredient in the solvent.

In another form of aqueous suspensions, a water-immiscible herbicide is encapsulated to form micrioencapsulated phase dispersed in an aqueous phase. In one embodiment, minute capsules are formed by bringing together an aqueous phase containing a lignin sulfonate emulsifier and a water-immiscible chemical and polymethylene polyphenylisocyanate, dispersing the water-immiscible phase in the aqueous phase followed by addition of a polyfunctional amine. The isocyanate and amine compounds react to form a solid urea shell wall around particles of the water-immiscible chemical, thus forming microcapsules thereof. Generally, the concentration of the microencapsulated material will range from about 480 to 700 g/l of total composition, preferably 480 to 600 g/l. The microencapsulation process referred to here is described in more detail in the assignee's copending U.S. Ser. No. 23,566 filed Mar. 26, 1979.

Concentrates are usually solutions of active ingredient in water-immiscible or partially water-immiscible solvents together with a surface active agent. Suitable solvents for the active ingredient of this invention include dimethylformide, dimethylsulfoxide, N-methylpyrrolidone, hydrocarbons and water-immiscible ethers, esters or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts preferably from about 3 to 20 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, othr pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles, biphenyl ethers and the like such as:

HETEROCYCLIC NITROGEN/SULFUR DERIVATIVES

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-c)-pyrazidiinium salt
5-Bromo-3-isopropyl-6-methyluracil
1,1'-Dimethyl-4,4'-bipyridinium

UREAS

N'-(4-chlorophenoxy)phenyl-N,N-dimethylurea
N,N-dimethyl-N'-(3-chloro-4-methylphenyl)urea
3-(3,4-dichlorophenyl)-1,1-dimethylurea
1,3-Dimethyl-3-(2-benzothiazolyl)urea
3-(p-Chlorophenyl)-1,1-dimethylurea
1-Butyl-3-(3,4-dichlorophenyl)-1-methylurea

CARBAMATES/THIOLCARBAMATES

2-Chloroallyl diethyldithiocarbamate
S-(4-chlorobenzyl)N,N-diethylthiolcarbamate
Isopropyl N-(3-chlorophenyl)carbamate
S-2,3-dichloroallyl N,N-diisopropylthiolcarbamate
Ethyl N,N-dipropylthiolcarbamate
S-propyl dipropylthiolcarbamate

ACETAMIDES/ACETANILIDES/ANILINES/AMIDES

2-Chloro-N,N-diallylacetamide
N,N-dimethyl-2,2-diphenylacetamide
N-(2,4-dimethyl-5-[[(trifluoromethyl)sulfonyl]amino]-phenyl)acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2-chloroacetanilide
Trifluoro-2,6-dinitro-N,N-dipropyl-p-toluidine
N-(1,1-dimethylpropynyl)-3,5-dichlorobenzamide

ACIDS/ESTERS/ALCOHOLS 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol
N-(phosphonomethyl)glycine and its $C_{1-6}$ *monoalkyl amine and alkaline metal salts and combinations thereof*

ETHERS 2,4-Dichlorophenyl-4-nitrophenyl ether
2-Chloro-α,α,α-trifluoro-p-tolyl-3-ethoxy-4-nitrodiphenyl ether

MISCELLANEOUS 2,6-Dichlorobenzonitrile
Monosodium acid methanearsonate
Disodium methanearsonate Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| | Weight Percent |
|---|---|
| I. Emulsifiable Concentrates | |
| A. Compound of Example No. 1 | 50.0 |
| Calcium dodecylbenzene sulfonate/polyoxyethylene ethers blend (e.g., Atlox ® 3437F and Atlox 3438F) | 5.0 |
| Monochlorobenzene | 45.0 |
| | 100.00 |
| B. Compound of Example No. 2 | 85.0 |
| Calcium dodecyl sulfonate/alkylaryl polyether alcohol blend | 4.0 |
| C₉ aromatic hydrocarbons solvent | 11.0 |
| | 100.00 |
| C. Compound of Example No. 3 | 5.0 |
| Calcium dodecylbenzene sulfonate/polyoxyethylene ethers blend (e.g., Atlox 3437F) | 1.0 |
| Xylene | 94.0 |
| | 100.00 |
| II. Liquid Concentrates | |
| A. Compound of Example No. 4 | 10.0 |
| Xylene | 90.0 |
| | 100.00 |
| B. Compound of Example No. 5 | 85.0 |
| Dimethyl sulfoxide | 15.0 |
| | 100.00 |
| C. Compound of Example No. 6 | 50.0 |
| N—methylpyrrolidone | 50.0 |
| | 100.00 |
| D. Compound of Example No. 7 | 5.0 |
| Ethoxylated castor oil | 20.0 |
| Rhodamine B | .5 |
| Dimethyl formamide | 74.5 |
| | 100.00 |
| III. Wettable Powders | |
| A. Compound of Example No. 8 | 25.0 |
| Sodium lignosulfonate | 3.0 |
| Sodium N—methyl-N—oleyl-taurate | 1.0 |
| Amorphous silica (synthetic) | 71.0 |
| | 100.00 |
| B. Compound of Example No. 1 | 80.0 |
| Sodium dioctyl sulfosuccinate | 1.25 |
| Calcium lignosulfonate | 2.75 |
| Amorphous silica (synthetic) | 16.00 |
| | 100.00 |
| C. Compound of Example No. 2 | 10.0 |
| Sodium lignosulfonate | 3.0 |
| Sodium N—methyl-N—oleyl-taurate | 1.0 |
| Kaolinite clay | 86.0 |
| | 100.0 |
| IV. Dusts | |
| A. Compound of Example No. 3 | 2.0 |
| Attapulgite | 98.0 |
| | 100.00 |
| B. Compound of Example No. 4 | 60.0 |
| Montmorillonite | 40.0 |
| | 100.00 |
| C. Compound of Example No. 5 | 30.0 |
| Bentonite | 70.0 |
| | 100.00 |
| D. Compound of Example No. 6 | 1.0 |
| Diatomaceous earth | 99.0 |
| | 100.00 |
| V. Granules | |
| A. Compound of Example No. 8 | 15.0 |
| Granular attapulgite (20/40 mesh) | 85.0 |
| | 100.00 |
| B. Compound of Example No. 1 | 30.0 |
| Diatomaceous earth (20/40) | 70.0 |
| | 100.00 |
| C. Compound of Example No. 2 | 0.5 |
| Bentonite (20/40) | 99.5 |
| | 100.00 |
| D. Compound of Example No. 3 | 5.0 |
| Pyrophyllite (20/40) | 95.0 |
| | 100.00 |

When operating in accordance with the present invention, effective amounts of the acetanilides of this invention are applied to the soil containing the plants, or are incorporated into aquatic media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds of this invention to the locus of undesired weeds is essential and critical for the practice of the present invention. The exact amount of active ingredient to be employed is dependent upon various factors, including the plant species and stage of development thereof, the type and condition of soil, the amount of rainfall and the specific acetanilide employed. In selective preemergence application to the plants or to the soil a dosage of from 0.02 to about 11.2 kg/ha, preferably from about 0.04 to about 5.60 kg/ha, or suitably from 1.12 to 5.6 kg/ha of acetanilide is usually employed. Lower or higher rates may be required in some instances. One skilled in the art can readily determine from this specification, including the above example, the optimum rate to be applied in any particular case.

The term "soil" is employed in its broadest sense to be inclusive of all conventional "soils" as defined in Webster's New International Dictionary, Second Edition, Unabridged (1961). Thus the term refers to any substance or media in which vegetation may take root and grow, and includes not only earth but also compost, manure, muck, humus, sand and the like, adapted to support plant growth.

Although the invention is described with respect to specific modifications, the details thereof are not to be construed as limitations except to the extent indicated in the following claims.

I claim:

1. Compounds having the formula

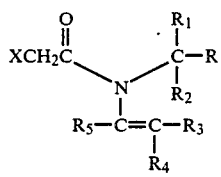

wherein X is chlorine, bromine or iodine;
$R_1$ and $R_2$ are hydrogen or $C_{1-6}$ alkyl;
$R_3$ and $R_4$ are an $R_1$ member or $C_{2-8}$ alkenyl or alkynyl radical;
$R_5$ is an $R_3$ member other than hydrogen, phenyl, benzyl, furyl, tetrahydrofuryl or said $R_5$ members substituted with an $R_3$ member, $C_{1-6}$ alkoxy, polyalkoxy, alkoxyalkyl, alkylthio, alkylthioalkyl, nitro, cyano, halogen, trifluoromethyl or hydroxy groups; and
R is phenyl or substituted phenyl radical as defined for $R_5$ or furyl when $R_5$ is phenyl or tolyl.

2. Herbicidal composition comprising an adjuvant and a herbicidally effective amount of a compound having the formula

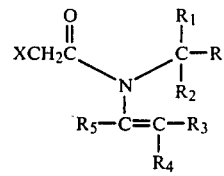

wherein X is chlorine, bromine or iodine;
$R_1$ and $R_2$ are hydrogen or $C_{1-6}$ alkyl;
$R_3$ and $R_4$ are an $R_1$ member or $C_{2-8}$ alkenyl or alkynyl radical;
$R_5$ is an $R_3$ member other than hydrogen, phenyl, benzyl, furyl, tetrahydrofuryl or said $R_5$ members substituted with an $R_3$ member, $C_{1-6}$ alkoxy, polyalkoxy, alkoxyalkyl, alkylthio, alkylthioalkyl, nitro, cyano, halogen, trifluoromethyl or hydroxy groups; and
R is phenyl or substituted phenyl radical as defined for $R_5$ or furyl when $R_5$ is phenyl or tolyl.

3. Method for combatting undesirable plants in crops which comprises applying to the locus thereof a herbicidally effective amount of a compound having the formula

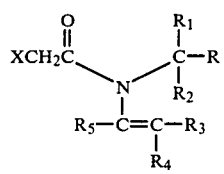

wherein X is chlorine, bromine or iodine;
$R_1$ and $R_2$ are hydrogen or $C_{1-6}$ alkyl;
$R_3$ and $R_4$ are an $R_1$ member or $C_{2-8}$ alkenyl or alkynyl radical;
$R_5$ is an $R_3$ member other than hydrogen, phenyl, benzyl, furyl, tetrahydrofuryl or said $R_5$ members substituted with an $R_3$ member, $C_{1-6}$ alkoxy, polyalkoxy, alkoxyalkyl, alkylthio, alkylthioalkyl, nitro, cyano, halogen, trifluoromethyl or hydroxy groups; and
R is phenyl or substituted phenyl radical as defined for $R_5$ or furyl when $R_5$ is phenyl or tolyl.

4. Compounds according to claim 2 wherein R is said furyl radical.

5. Compounds according to claim 4 wherein $R_5$ is said phenyl or substituted phenyl radical.

6. Compound according to claim 3 wherein $R_5$ is a $C_{1-6}$ alkyl radical.

7. Compound according to claim 5 which is N-furfuryl-N-(1-o-tolyl propen-1-yl)-2-chloroacetamide.

8. Compound according to claim 6 which is N-(4-methoxybenzyl)-N-(2-methyl-2-buten-3-yl)-2-chloroacetamide.

9. Herbicidal composition comprising an adjuvant and a herbicidally effective amount of a compound having the formula

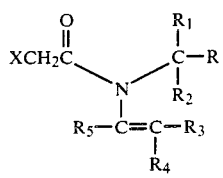

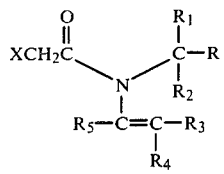

wherein X is chlorine, bromine or iodine;
$R_1$ and $R_2$ are hydrogen or $C_{1-6}$ alkyl;
$R_3$ and $R_4$ are an $R_1$ member or $C_{2-8}$ alkenyl or alkynyl radical;
$R_5$ is an $R_3$ member other than hydrogen, phenyl, benzyl, furyl, tetrahydrofuryl or said $R_5$ members substituted with an $R_3$ member, $C_{1-6}$ alkoxy, polyalkoxy, alkoxyalkyl, alkylthio, alkylthioalkyl, nitro, cyano, halogen, trifluoromethyl or hydroxy groups; and
R is a furyl, tetrahydrofuryl, phenyl or substituted phenyl radical as defined for $R_5$; provided that when R is furyl or tetrahydrofuryl radical, $R_5$ is other than hydrogen, alkyl or alkenyl.

10. Composition according to claim 9 wherein in said compound $R_1$, $R_2$, $R_3$ and $R_4$ are independently hydrogen or $C_{1-6}$ alkyl.

11. Composition according to claim 10 wherein in said compound R is said phenyl or substituted phenyl radical.

12. Composition according to claim 10 wherein in said compound R is said furyl radical.

13. Composition according to claim 12 wherein in said compound $R_5$ is said phenyl or substituted phenyl radical.

14. Composition according to claim 11 wherein in said compound $R_5$ is a $C_{1-6}$ alkyl radical.

15. Composition according to claim 13 wherein said compound is N-furfuryl-N-(1-o-tolyl propen-1-yl)-2-chloroacetamide.

16. Composition according to claim 14 wherein said compound is N-(4-methoxybenzyl)-N-(2-methyl-2-buten-3-yl)-2-chloroacetamide.

17. Method for combatting undesirable plants in crops which comprises applying to the locus thereof a herbicidally effective amount of a compound having the formula wherein X is chlorine, bromine or iodine;
$R_1$ and $R_2$ are hydrogen or $C_{1-6}$ alkyl;
$R_3$ and $R_4$ are an $R_1$ member of $C_{2-8}$ alkenyl or alkynyl radical;
$R_5$ is an $R_3$ member other than hydrogen, phenyl, benzyl, furyl, tetrahydrofuryl or said $R_5$ members substituted with an $R_3$ member, $C_{1-6}$ alkoxy, polyalkoxy, alkoxyalkyl, alkylthio, alkylthioalkyl, nitro, cyano, halogen, trifluoromethyl or hydroxy groups; and
R is a furyl, tetrahydrofuryl, phenyl or substituted phenyl radical as defined for $R_5$; provided that when R is furyl or tetrahydrofuryl radical, $R_5$ is other than hydrogen, alkyl or alkenyl.

18. Method according to claim 17 wherein in said compound $R_1$, $R_2$, $R_3$ and $R_4$ are independently hydrogen or $C_{1-6}$ alkyl.

19. Method acording to claim 18 wherein in said compound R is said phenyl or substituted phenyl radical.

20. Method according to claim 18 wherein in said compound R is said furyl radical.

21. Method according to claim 20 wherein in said compound $R_5$ is said phenyl or substituted phenyl radical.

22. Method according to claim 19 wherein in said compound $R_5$ is a $C_{1-6}$ alkyl radical.

23. Method according to claim 19 wherein said compound is N-furfuryl-N-(1-o-tolyl propen-1-yl)-2-chloroacetamide.

24. Method according to claim 22 wherein said compound is N-(4-methoxybenzyl)-N-(2-methyl-2-buten-3-yl)-2-chloroacetamide.

25. Compound according to claim 6 which is N-(o-methoxybenzyl)-N-(2-methyl-2-buten-3-yl)-2-chloroacetamide.

26. Composition according to claim 14 wherein said compound is N-(o-methoxybenzyl)-N-(2-methyl 2-buten-3-yl)-2-chloroacetamide.

27. Method according to claim 22 wherein said compound is N-(o-methoxybenzyl)-N-(2-methyl-2-buten-3-yl)-2-chloroacetamide.

* * * * *